US011511046B2

(12) United States Patent
Knudsen et al.

(10) Patent No.: US 11,511,046 B2
(45) Date of Patent: Nov. 29, 2022

(54) PREFILLED DRUG DELIVERY DEVICE WITH REDUCED AIR GAP

(71) Applicant: Novo Nordisk A/S, Bagsvaerd (DK)

(72) Inventors: Daniel Knudsen, Farum (DK); Jeppe Marckmann, Kastrup (DK)

(73) Assignee: Novo Nordisk A/S, Bagsvaerd (DK)

( * ) Notice: Subject to any disclaimer, the term of this patent is extended or adjusted under 35 U.S.C. 154(b) by 281 days.

(21) Appl. No.: 16/754,982

(22) PCT Filed: Oct. 9, 2018

(86) PCT No.: PCT/EP2018/077442
§ 371 (c)(1),
(2) Date: Apr. 9, 2020

(87) PCT Pub. No.: WO2019/072826
PCT Pub. Date: Apr. 18, 2019

(65) Prior Publication Data
US 2021/0196898 A1 Jul. 1, 2021

(30) Foreign Application Priority Data
Oct. 10, 2017 (EP) ..................................... 17195670

(51) Int. Cl.
*A61M 5/315* (2006.01)
*A61M 5/20* (2006.01)
*A61M 5/24* (2006.01)

(52) U.S. Cl.
CPC ...... *A61M 5/31551* (2013.01); *A61M 5/2033* (2013.01); *A61M 5/24* (2013.01); *A61M 5/31515* (2013.01); *A61M 5/31526* (2013.01); *A61M 5/31528* (2013.01); *A61M 5/31543* (2013.01); *A61M 5/31585* (2013.01)

(58) Field of Classification Search
CPC .. A61M 5/31551; A61M 5/2033; A61M 5/24; A61M 5/31515; A61M 5/31526; A61M 5/31528; A61M 5/31543; A61M 5/31585
See application file for complete search history.

(56) References Cited

U.S. PATENT DOCUMENTS

| 5,226,895 | A | * | 7/1993 | Harris | ............... A61M 5/31591 |
| | | | | | 604/218 |
| 9,138,543 | B2 | | 9/2015 | Frantz et al. | |
| 9,592,347 | B2 | | 3/2017 | Nzike et al. | |
| 9,649,446 | B2 | | 5/2017 | Wieselblad | |
| 10,058,659 | B2 | | 8/2018 | Saiki | |

(Continued)

FOREIGN PATENT DOCUMENTS

| JP | 2008515471 A | 5/2008 |
| WO | 9938554 | 8/1999 |

(Continued)

*Primary Examiner* — Dung T Ulsh
(74) *Attorney, Agent, or Firm* — Wesley Nicolas

(57) ABSTRACT

A method of assembling a drug delivery device, comprising the steps of: inserting a piston rod in a nut portion of a cartridge assembly and rotating the piston rod until the piston rod distal end engages the cartridge piston, mounting a drive member on the piston rod in a rota-tional position being closest to a pre-determined rotational position, and rotating the drive member to the pre-determined rotational position.

13 Claims, 3 Drawing Sheets

(56) References Cited

U.S. PATENT DOCUMENTS

| | | | |
|---|---|---|---|
| 10,245,386 B1* | 4/2019 | Berenshteyn | A61M 5/31515 |
| 2016/0067416 A1 | 3/2016 | Holtwick et al. | |
| 2016/0271332 A1 | 9/2016 | Bilton | |
| 2016/0317751 A1* | 11/2016 | Andersen | A61M 5/20 |
| 2016/0361498 A1 | 12/2016 | Markus | A61M 5/31536 |
| 2017/0340830 A1* | 11/2017 | Wieselblad | A61M 5/31535 |
| 2018/0221587 A1* | 8/2018 | Keitel | A61M 5/31553 |
| 2019/0224412 A1* | 7/2019 | Stefanski | A61M 5/31553 |
| 2019/0290851 A1 | 9/2019 | Eich et al. | |
| 2019/0358407 A1* | 11/2019 | Hewson | A61M 5/24 |

FOREIGN PATENT DOCUMENTS

| | | |
|---|---|---|
| WO | 01/19434 A1 | 3/2001 |
| WO | 2006076921 | 7/2006 |
| WO | 2006/128794 | 12/2006 |
| WO | 200910599 | 1/2009 |
| WO | 2009095332 A1 | 8/2009 |
| WO | 2009105909 A1 | 9/2009 |
| WO | 2009/132777 A1 | 11/2009 |
| WO | 2010029043 A1 | 3/2010 |
| WO | 2010149209 A1 | 12/2010 |
| WO | 2014166893 | 10/2014 |
| WO | 2015032782 | 3/2015 |
| WO | 2016055625 | 4/2016 |
| WO | 2016102526 | 6/2016 |
| WO | 2018007623 | 1/2018 |

\* cited by examiner

Fig. 4A
Fig. 4B
Fig. 4C
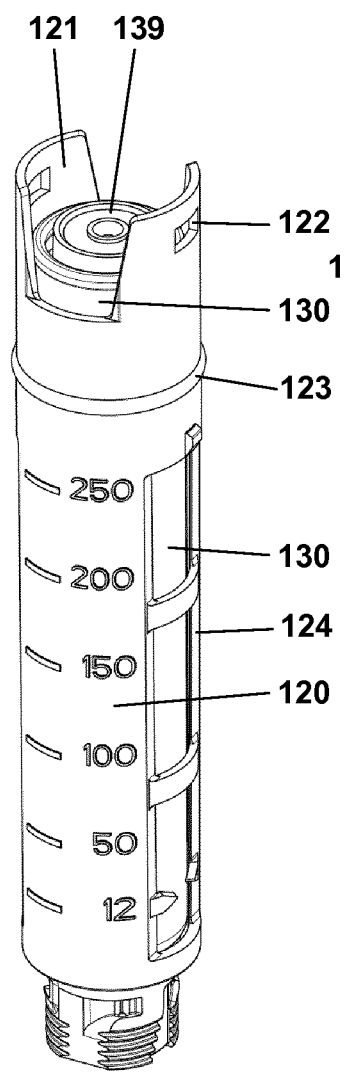
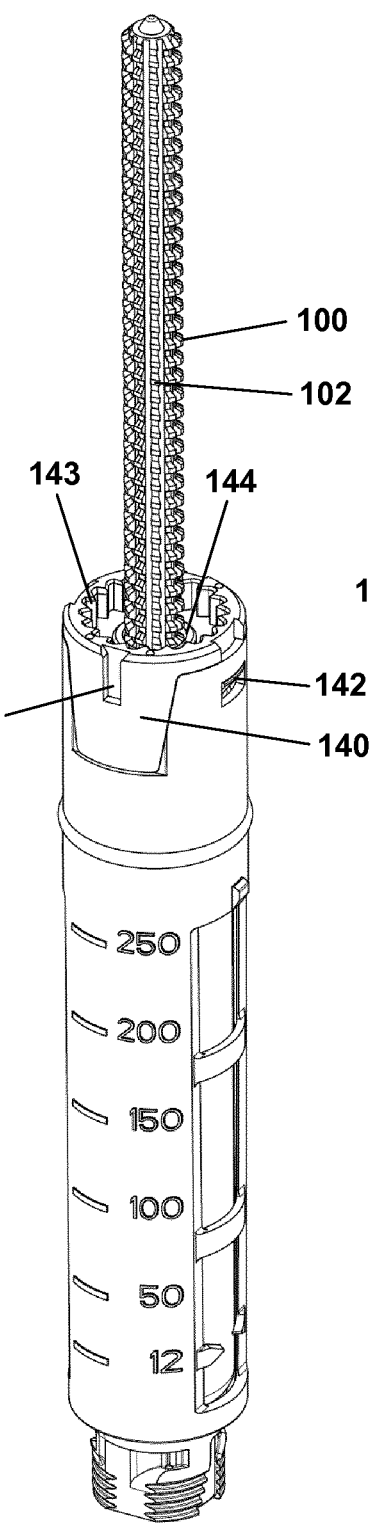
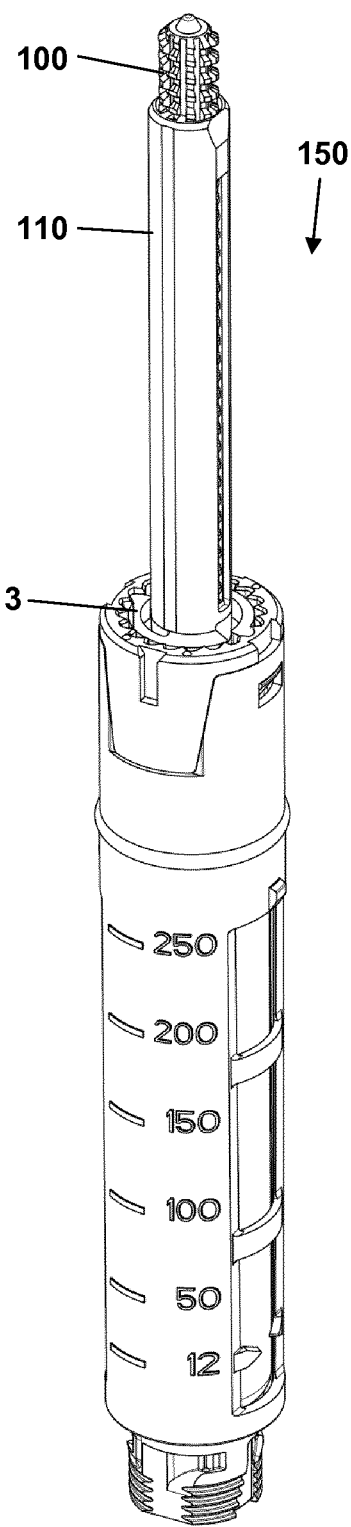

PREFILLED DRUG DELIVERY DEVICE WITH REDUCED AIR GAP

CROSS-REFERENCE TO RELATED APPLICATIONS

This application is a 35 U.S.C. § 371 National Stage application of International Application PCT/EP2018/077442 (published as WO 2019/072826), filed Oct. 9, 2018, which claims priority to European Patent Application 17195670.9, filed Oct. 10, 2017; the contents of which are incorporated herein by reference.

The present invention generally relates to drug delivery devices and methods for their assembly, the devices being adapted to be used and operated by a patient on his or her own hand. In specific embodiments the invention relates to medical delivery devices of the pre-filled type as well as to methods of their assembly.

BACKGROUND OF THE INVENTION

In the disclosure of the present invention reference is mostly made to the treatment of diabetes by delivery of insulin or other diabetes drugs, however, this is only an exemplary use of the present invention.

Drug delivery devices in the form of injection devices for subcutaneous administration of fluid drugs have greatly improved the lives of patients who must self-administer drugs and biological agents. Drug injection devices may take many forms, including simple disposable devices that are little more than an ampoule with an injection means or they may be highly sophisticated electronically controlled instruments with numerous functions. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. Typically, injection devices use a pre-filled cartridge containing the medication of interest, e.g. 1.5 or 3.0 ml of insulin or growth hormone. The cartridge is typically in the form of a generally cylindrical transparent ampoule with a needle pierceable septum at one end and an opposed piston designed to be moved by the dosing mechanism of the injection device. The injection devices generally are of two types: "Durable" devices and "disposable" devices. A durable device, see e.g. WO 2009/10599 and WO 2009/132777, is designed to allow a user to replace one cartridge with another cartridge, typically a new cartridge in place of an empty cartridge. In contrast, a disposable (or "prefilled") device is provided with an integrated cartridge which cannot be replaced by the user without damaging or destroying the device; when the cartridge is empty the entire device is to be discarded.

A further distinction can be made for the drive means delivering the force to move the cartridge piston forwards during expelling of a dose of drug. Traditionally injection devices have been manually actuated by the user pushing an extendable button during expelling, however, alternatively the driving force may be provided by a spring being pre-strained or strained during dose setting and subsequently released, this allowing for "automatic" dispensing of drug.

Although some injection devices are designed for delivery of a fixed dose, either a single fixed dose corresponding to the amount of drug in the cartridge or a number of fixed doses from a larger cartridge, the majority of injection devices comprises dose setting means allowing a user to set a desired size for the dose of drug to be expelled.

As mentioned above, a liquid drug to be administered is typically provided in a cartridge having a moveable piston mechanically interacting with a piston rod of an expelling mechanism of a drug delivery device. By applying thrust to the piston in distal direction, a given set amount of the liquid drug can be expelled from the cartridge. A prefilled drug delivery device will typically be provided to the user with an axial clearance (or "air gap") between the cartridge's piston and the piston rod, this being due to inevitable manufacturing tolerances, the actual design of the expelling mechanism as well as the assembly process.

Correspondingly, prior to a primary use of the device, an end-user has to conduct a so-called priming of the expelling mechanism in order to ensure that the piston rod is brought into contact with the cartridge piston, such that already with an initial dose setting and a first subsequent dose dispensing step, an accurate amount of the liquid drug is dispensed in a predefined way. An initial dose setting and expelling of a minor dose may in certain situations also be required for removing any air present in the cartridge and/or a connected needle and for performing a flow check. WO 99/38554 discloses several embodiments of drug delivery devices each suitable for forming a disposable device wherein a liquid drug cartridge is inserted into the device during assembly in a production line.

State of the art pen-type drug delivery devices that incorporate a dose setting feature often include a so-called end-of-content (EoC) member to prevent a user from selecting a size of a dose which exceeds the amount of liquid drug remaining in a cartridge of the device, see e.g. WO 01/19434, WO 2006/128794 and WO 2010/149209. In its initial position the EoC member will allow a pre-defined amount of drug to be expelled before the dose setting mechanism will be blocked, e.g. 300 IU of insulin corresponding to 3 ml of drug formulation. However, when one or more priming steps is performed initially to remove the air gap the EoC member will "count down" correspondingly, this preventing the full and intended amount of useable drug to be expelled from the cartridge. Further, air gap removal will result in variations in the amount of drug delivered to the end-user as the amount of "doses" needed for removal of the air gab varies based on the size of the actual air gap in a given device.

WO 2014/16689 discloses a drive mechanism for a drug delivery device in which the piston is advanced axially by rotation of drive nut in threaded engagement only with the piston rod. As the drive nut can be mounted on the piston rod in any rotational position, this design allows the piston rod during manufacturing to be advanced into contact with the cartridge piston and the drive nut to be subsequently mounted in the desired axial position. However, for a piston rod comprising a "sliding" drive system, e.g. comprising a slotted piston rod, which is designed for a specific rotational mounting position this is not possible.

Having regard to the above, it is an object of the present invention to provide in a cost-effective manner a drug delivery device of the prefilled type comprising a drive system of the sliding type, as well as components therefore, with only a minimal (ideally no) initial air gap between the piston driving member of the expelling mechanism, e.g. a piston rod, and the cartridge piston.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect of the invention a method of assembling a cartridge-piston rod sub-assembly for a drug delivery device is provided, comprising the steps of (i) providing an assembly comprising a cartridge with an axially displaceable piston, the piston comprising a proximally facing free surface, a cartridge holder in which the cartridge is arranged, and a nut portion arranged proximally of the piston and comprising a threaded bore, (ii) providing a threaded piston rod comprising at least one outer drive structure and a distal end, (iii) providing a drive member comprising at least one inner drive structure, the number and circumferential spacing of the outer and inner drive structures allowing the piston rod to be axially received in at least three different rotational positions in which the piston rod and drive member are in axially sliding but rotationally locked engagement, the drive member having at least one pre-determined rotational position relative to the cartridge holder, (iv) inserting the piston rod in the nut portion threaded bore and rotating the piston rod until the piston rod distal end engages, directly or indirectly, the cartridge piston, (v) mounting the drive member on the piston rod in the rotational position being closest to a pre-determined rotational position, and (vi) rotating the drive member to the pre-determined rotational position.

When it is defined that the drive member is mounted on the piston rod in the rotational position being closest to a pre-determined rotational position, this incorporates the desired or allowed direction of subsequent rotational movement. For example, if the drive member can be mounted on the piston rod in rotational positions with a spacing of 30 degrees, then both a rotational position 5 degrees off-set in one direction and a rotational position 25 degrees offset in the opposite direction may be considered "being closest" to a pre-determined rotational position. The relevance of these options is described below.

By this arrangement a drug delivery device can be provided in which an initial air gap between the piston rod distal end and the cartridge piston can be reduced. Indeed, the more drive structures are provided circumferentially on the piston rod surface, the more possible rotatable positions the drive member can be mounted in, this minimizing the amount of rotation needed to rotate the drive member to a pre-determined rotational position.

The drive structures can be provided in variety of configurations full-filing the required specification of allowing the piston rod to be axially received in at least three different rotational positions in which the piston rod and drive member are in axially sliding but rotationally locked engagement. For example, the piston rod may comprise at least three outer drive structures and the drive member may comprise at least one inner drive structure. Alternatively the piston rod may comprise at least one outer drive structure and the drive member may comprise at least three inner drive structures. As a further alternative the piston rod comprises at least three outer drive structures and also the drive member comprises at least three inner drive structures.

In order to allow the piston rod and drive member to slide axially relative to each other and allow the drive structure to transfer rotational movement, the outer drive structure(s), the inner drive structure(s), or both the outer and inner drive structure(s) may have a longitudinal configuration.

The drive structures may be arranged equidistantly on the piston rod outer surface, and may be provided in an even number as opposed pairs.

It is to be noted that the present invention does not relate to the assembly of a drug delivery device in its entirety but only to a portion of such an assembly process as any remaining assembling steps will be determined by the actual design of a given drug delivery device, this being outside the scope of the present invention.

In the final step the drive member may be rotated to further advance the piston rod when rotated to a pre-determined rotational position, this providing an assembly in which an air gap has been fully eliminated. As appears, this would result in pressurization of the cartridge which to a certain extent may be acceptable. Alternatively the drive member may be rotated in the opposite direction to retract the piston rod when rotated to a pre-determined rotational position.

Depending on the number of pre-determined rotational position for a given assembly it may be desirable for each individual assembly to be able to decide whether to move the piston rod distally and thereby pressurize the cartridge, or to move the piston rod proximally and thereby create an air gap, e.g. by using a vision system.

In an exemplary embodiment the drive member has a first axial position in which the drive member is freely rotatable relative to the cartridge holder, and a second axial position in which the drive member is rotationally locked relative to the cartridge holder. The locking may be "absolute" preventing rotation or it may be relative preventing rotation up to a certain amount of applied rotational force. In this way it can be prevented to a certain degree that the drive member can rotate relative to the cartridge holder during subsequent assembling steps, e.g. when an additional component is mounted in engagement with the drive member.

In an exemplary embodiment the rotational lock is provided by a one-way ratchet arranged between the drive member and the nut portion preventing rotation of the drive member relative to the nut portion in a first direction, and allowing rotation in the opposite direction when a certain force limit is exceeded. The nut portion may be in the form of a nut member attached non-rotationally to the cartridge holder.

In a second aspect of the invention a drug delivery device is provided comprising a cartridge, a housing, and an expelling arrangement comprising a piston rod, a nut portion and a drive member. The cartridge comprises a cylindrical body portion defining an axial orientation, an outlet portion and an axially displaceable piston. The expelling arrangement comprises a piston rod, a nut portion and a drive member. The piston rod is adapted to engage and axially displace the cartridge piston in a distal direction to thereby expel a dose of drug from the cartridge, the piston rod comprising an outer thread and at least one outer drive structure. The piston rod may engage and axially displace the cartridge piston directly or indirectly, e.g. without or with a piston washer. The nut portion is non-rotationally coupled to the housing and comprises a threaded bore receiving the piston rod in threaded engagement. The drive member, in which the piston rod is arranged, comprises at least one inner drive structure, the number and circumferential spacing of the outer and inner drive structures allowing the piston rod to be mounted in at least three different rotational positions in which the piston rod and drive member are in axially sliding but rotationally locked engagement. The drug delivery device further comprises a drive arrangement allowing a user to rotate the drive member to thereby expel an amount of drug from the cartridge as the piston rod is rotated and moved axially through the nut portion.

By this arrangement a drug delivery device is provided in which an initial air gap between the piston rod distal end and the cartridge piston can be reduced, this as describe above with reference to the method aspect of the present invention.

The drive structures can be provided in variety of configurations full-filing the required specification of allowing the piston rod to be axially received in at least three different rotational positions in which the piston rod and drive member are in axially sliding but rotationally locked engagement. For example, the piston rod may comprise at least three outer drive structures and the drive member may comprise at least one inner drive structure. Alternatively the piston rod may comprise at least one outer drive structure and the drive member may comprise at least three inner drive structures. As a further alternative the piston rod comprises at least three outer drive structures and also the drive member comprises at least three inner drive structures.

In order to allow the piston rod and drive member to slide axially relative to each other and allow the drive structure to transfer rotational movement, the outer drive structure(s), the inner drive structure(s), or both the outer and inner drive structure(s) may have a longitudinal configuration.

The drive structures may be arranged equidistantly on the piston rod outer surface, and may be provided in an even number as opposed pairs.

It is to be noted that the present invention does not relate to a drug delivery device in its entirety but only to a portion of such a device as any additional components will be determined by the actual design of a given drug delivery device, this being outside the scope of the present invention.

In an exemplary embodiment the expelling arrangement further comprises a dose setting member rotatable from an initial position to a set position corresponding to a set dose, and an actuation member actuatable to rotate the drive member corresponding to the set dose. The actuation member may be arranged to be moved proximally during dose setting from an initial position to a set position corresponding to the rotationally set dose, wherein the actuation member is actuatable by axial movement from the set position to the initial position.

The expelling arrangement may further comprise a drive spring strained during dose setting corresponding to the set dose, wherein the drive spring is released to rotate the drive member corresponding to the set dose when the actuation member is actuated.

The outer and inner drive structures may be in the form of corresponding spline structures. Alternatively, the outer and inner drive structures may be in the form of corresponding primarily planar surfaces, i.e. the drive surfaces may incorporate additional structures provided for e.g. manufacturing or functional reasons.

In an exemplary embodiment a one-way ratchet is arranged between the drive member and the nut portion preventing rotation of the drive member relative to the nut portion in a first direction, and allowing rotation in the opposite direction when a certain force limit is exceeded.

In a further aspect of the invention a cartridge-piston rod sub-assembly for a drug delivery device is provided, comprising a cartridge with an axially displaceable piston, the piston comprising a proximally facing free surface, a cartridge holder in which the cartridge is arranged, a nut portion non-rotationally coupled to the cartridge holder and comprising a threaded bore adapted to receive the piston rod in threaded engagement, and a piston rod.

The piston rod is received in the threaded bore and adapted to engage and axially displace, directly or indirectly, the cartridge piston in a distal direction to thereby expel a dose of drug from the cartridge, the piston rod comprising an outer thread, and at least one outer drive structure, a drive member in which the piston rod is arranged, comprising at least one inner drive structure, the number and circumferential spacing of the outer and inner drive structures allowing the piston rod to be mounted in at least three different rotational positions in which the piston rod and drive member are in axially sliding but rotationally locked engagement.

As used herein, the term "drug" is meant to encompass any drug-containing flowable medicine capable of being passed through a delivery means such as a cannula or hollow needle in a controlled manner, such as a liquid, solution, gel or fine suspension. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin containing drugs. Correspondingly, the term "subcutaneous" infusion is meant to encompass any method of transcutaneous delivery to a subject.

BRIEF DESCRIPTION OF THE DRAWINGS

In the following the invention will be further described with reference to the drawings, wherein FIGS. 4A-4C show steps of an assembly procedure incorporating the components of the assembly of FIG. 3A.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to an embodiment of the present invention per se, an example of a prefilled drug delivery device will be described, such a device providing a basis for the exemplary embodiment of the present invention. The described device corresponds to the drug delivery device disclosed in FIGS.

16 and 17 of WO 99/38554, and conceptually represents a Flex-Pen® drug delivery device as sold and manufactured by Novo Nordisk A/S, Denmark.

Figure 1:
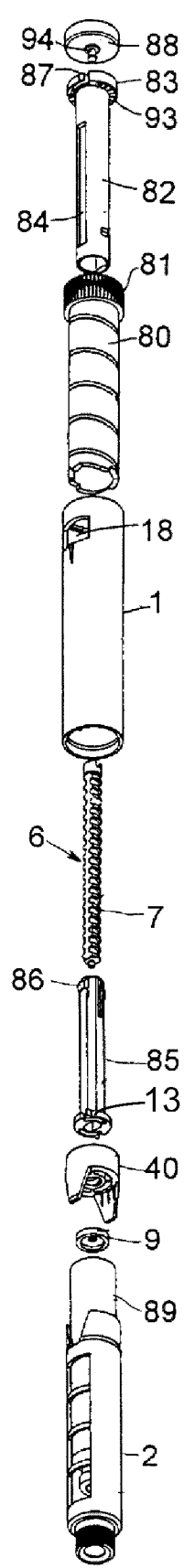
FIG. 1 shows in an exploded view the components of a drug delivery device.

FIG. 1 shows in an exploded view the components of a prefilled drug delivery device, comprising a distal group of components which during the manufacturing process is assembled to a cartridge sub-assembly, as well as a proximal group of components which during the manufacturing process is assembled to a driver sub-assembly, the two sub-assemblies being mounted to each other in a final manufacturing step to provide the finished product (excluding the not-shown cap).

The cartridge sub-assembly comprises a cartridge holder 2 adapted to receive a drug-filled cartridge 89, a nut member 40 with a threaded bore portion 4 and an inner circumferential array of ratchet protrusions, a piston washer 9, a piston rod 6 comprising an outer thread 7 adapted to engage the threaded nut bore as well as a pair of opposed planar drive surfaces, and a ratchet drive tube 85. The ratchet drive tube 85 comprises a bore with an inner pair of opposed planar drive surfaces adapted to be arranged in sliding non-rotational engagement with the piston rod drive surfaces, a pair of opposed distally arranged ratchet arms 13 adapted to engage the nut member ratchet array, as well as a pair of opposed proximally arranged hook portions 86 adapted to engage the connector tube 82 (see below). The cartridge holder comprises a pair of opposed inspection windows allowing a user to inspect the cartridge.

The driver sub-assembly comprises a tubular housing 1 with a window 18 and a distal circumferential inner flange portion 46, a scale drum 80 with a proximal dose setting gripping portion 81 (or "dose setting button") having an inner compartment and an outer helical groove adapted to engage a helical rib on the inner housing surface, a connector tube 82 comprising a proximal clutch portion 83 as well as a pair of opposed slots 84 adapted to axially engage the ratchet tube hook portions 86 whereby the connector tube 82 and the ratchet drive tube 85 is coupled to each other so that rotation but not longitudinal displacement is transmitted between said two elements, and an expelling push button member 90 with a pivot pin 94 adapted to be rotatably mounted in the connector tube proximal end. Numbers indicating set doses are printed on the outer wall of the scale drum 80 and the number corresponding to a set dose is shown in a window 18 provided in the side wall of the housing 1.

In the dose setting gripping portion 81 a compartment is provided having a cylindrical side wall circumferentially provided with longitudinal recesses and a bottom with a rosette of teeth having a triangular cross-section. The clutch portion 83 of the connector tube 82 can be seated in said compartment and has at its periphery a flexible clicker arm with a radial protrusion 87 which is biased toward the side wall of the compartment. Distally the clutch portion 83 has a rosette 93 of teeth which can be brought into engagement with the rosette at the bottom of the compartment. In an alternative embodiment (not shown) as used in the Flex-Pen® the proximal clicker portion and the remaining portion of the connector tube may be formed as two components (see below).

The connector tube 82 can be mounted in the scale drum 80 with protrusion on the outer wall of the connector tube 82 engaging recesses in the inner wall of the scale drum 80 so that a limited movement of the connector tube in the scale drum is allowed so that the connector tube can be moved axially relative to the scale drum to make or not make the teeth of said rosettes engage each other.

In a preferred embodiment the driver sub-assembly comprises an EoC member (not shown) preventing that a dose larger than the remaining amount of drug in the cartridge can be set, see WO 01/19434 in which the functionality of the EoC feature is described in detail. In summary, the ring-formed EoC member comprises an inner thread adapted to be mounted in threaded engagement with an outer EoC thread on the connector tube (not shown) and an outer spline adapted to engage a corresponding spline structure on the scale drum inner surface. In this way relative rotation between the connector tube and the scale drum will result in the EoC member being moved axially on the connector tube, i.e. from an initial distal-most position to an end-of-content final position in engagement with proximal stop structures on the connector tube.

When a dose is set by rotating the dose setting button 81 in a clockwise direction, the scale drum is screwed out of the housing and the dose setting button is lifted away from the proximal end of the housing. The connector tube 82 is kept non-rotated due to its coupling to the ratchet drive tube 85 which is locked against clockwise rotation and if a set dose is reduced by rotating the dose setting button 81 in an anticlockwise direction the ratchet mechanism 13 working between the ratchet drive tube 85 and the nut member 40 is sufficient reluctant to rotate in its non-blocking direction to prevent the connector tube 82 from following this anti-clockwise rotation. Therefore by the rotation of the dose setting button 81 in any direction the radial protrusion 87 on the clutch portion 83 of the connector tube 82 will click from one of the axial recess in the inner wall of the dose setting button 81 to the next one, the recesses being so spaced that one click corresponds to a given incremental change of the set dose, e.g. one unit or a half unit. During dose setting the rosette in the dose setting button forces the rosette 93 on the clutch portion 83 of the connector tube 82 out of engagement.

When the expelling button 90 is depressed to expel the set dose the said rosettes are forced into engagement so that the connector tube 82 will follow the anticlockwise rotation of the dose setting button 81 which is induced by the thread engagement between the helical track of the scale drum 80 and the rib 16 (see FIG. 2) in the housing when the scale drum 80 is moved back into the housing 1. The connector tube 82 will rotate the ratchet drive tube 85 in an anticlockwise direction overcoming the resistance in the ratchet mechanism 13, 40 whereby the piston rod 7 is rotated further into cartridge 89 in the cartridge holder 2. At the same time the ratchet generates a series of expelling clicks.

As mentioned above, in an alternative embodiment as used in the FlexPen® the proximal clicker portion is formed as a separate member. More specifically, the separate clicker member comprises a proximal set of opposed ratchet dose setting clicker arms uni-directionally engaging an array of ratchet teeth on the inner circumferential wall of the dose setting button 81, as well as a distal pair of opposed ratchet dose setting clicker arms uni-directionally engaging an array of ratchet teeth on the connector tube clutch portion 83 inner wall. When setting a dose the proximal set of clicker arms will generate dose clicks, whereas when reducing a set dose the distal ratchet arms will generate dose clicks.

When assembling the cartridge sub-assembly, the piston rod and the ratchet tube may be mounted to the nut member before being attached to the cartridge holder, this allowing the ratchet member to be mounted in a predefined rotational position relative to the cartridge holder. More specifically, the piston rod 6 is threaded through the nut bore until the piston rod has been axially positioned corresponding to an expected proximal-most position of the cartridge piston and with the piston rod in a predefined rotational position relative to the nut member 40. Next the ratchet tube 85 is slid over the piston rod until the ratchet arms engage the nut member ratchet array. Due to the cooperating drive surfaces between the piston rod and the ratchet tube also the latter will be arranged in a predefined rotational position. Finally the cartridge 89 is inserted into the cartridge holder 2, the piston washer 9 is arranged on top of the cartridge piston, and the nut member 40 with the mounted piston rod and ratchet tube is snapped into engagement with the cartridge holder. As the piston rod has been axially positioned corresponding to an expected proximal-most position of the cartridge piston, this will in most cases result in an air gap between the piston rod and the piston washer.

Alternatively, the cartridge 89 is first inserted into the cartridge holder 2, the piston washer 9 is arranged on top of the cartridge piston, and the nut member 40 is snapped into engagement with the cartridge holder. Next the piston rod 6 is threaded through the nut bore until it engages the piston washer. As a final step the ratchet tube 85 is slid over the piston rod until the ratchet arms adapted engage the nut member ratchet array. As the axial position of the cartridge piston varies due to manufacturing tolerances also the rotational position of the piston rod and thereby the rotational position of the ratchet tube relative to the cartridge holder would vary for the assembled cartridge sub-assembly. However, as will be described below, when assembling the two sub-assemblies the ratchet tube will have to be arranged in one of two predefined and 180 degrees off-set rotational positons. Correspondingly, before seating the ratchet arms in the nut member ratchet array the ratchet tube will have to be rotated to one of the two pre-defined rotational positions, this resulting in an air gap being introduced between the piston rod and the piston washer.

When assembling the driver sub-assembly first the scale drum 80 is inserted into the housing 1 and rotated to its distal-most position with the numeral "0" arranged in the housing window 18. Next the EoC member is inserted axially into the scale drum and seated corresponding to its initial distal-most position, after which the connector tube is inserted and seated in the scale drum in a predefined rotational position relative to the cartridge holder and thus the housing, the outer EoC thread just engaging the EoC member. In this way the pair of opposed slots 84 on the connector tube adapted to axially engage the ratchet tube hook portions 86 are positioned in a predefined rotational position relative to the housing. If the clutch portion 83 is a separate member it may be mounted now or later.

A snap coupling is provided between the two sub-assemblies allowing the driver sub-assembly to be mounted on the cartridge sub-assembly in one of two predefined and 180 degrees off-set rotational positons with the housing window 18 in rotational alignment with one of the two cartridge inspection windows. During this assembly step the opposed ratchet tube hook portions 86 will have to snap into engagement with the connector tube opposed slots 84. Indeed, to allow this the ratchet tube and the connector tube have to be arranged in one of two predefined and 180 degrees off-set rotational positons relative to each other, this as described above. In the assembled state the ratchet arms 13 (and thus the ratchet tube 85) are arranged between the nut member bore portion 4 and the housing inner flange 46, this preventing axial movement of the ratchet tube 85 yet allows it to rotate. As a final step before attaching the cap the separate clutch member (if provided) is mounted and the dose button 88 is snapped in place.

Figure 2:
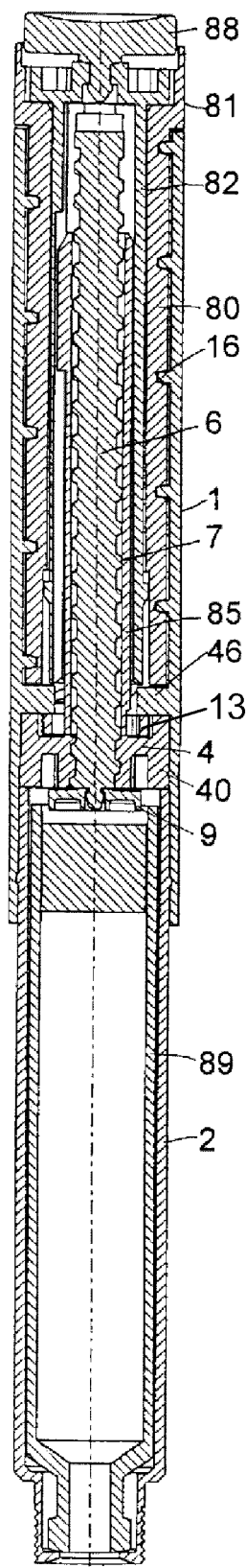
FIG. 2 shows in a cross-sectional view the drug delivery device of FIG. 1 in an assembled state.

FIG. 2 shows in a cross-sectional view the drug delivery device in an assembled state.

Figure 3A:
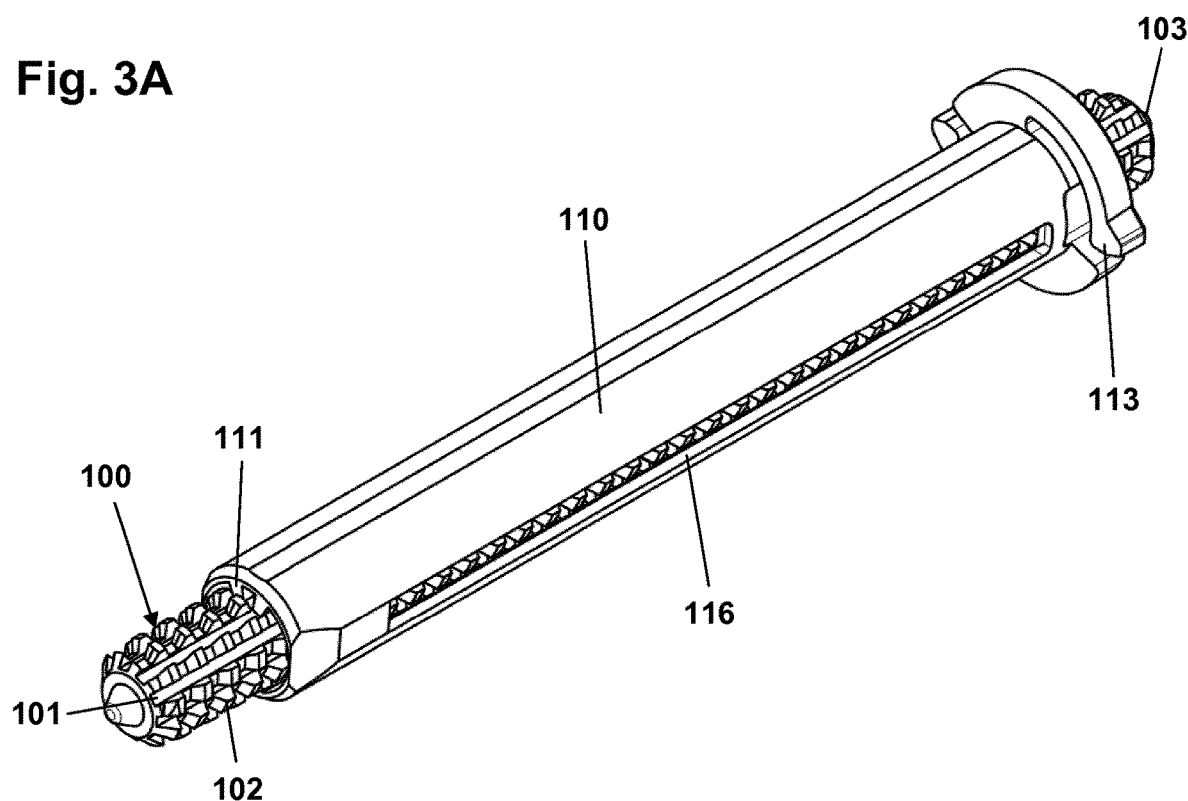
FIGS. 3A and 3B show an assembly of a modified piston rod and a correspondingly modified ratchet tube.
Figure 3B:
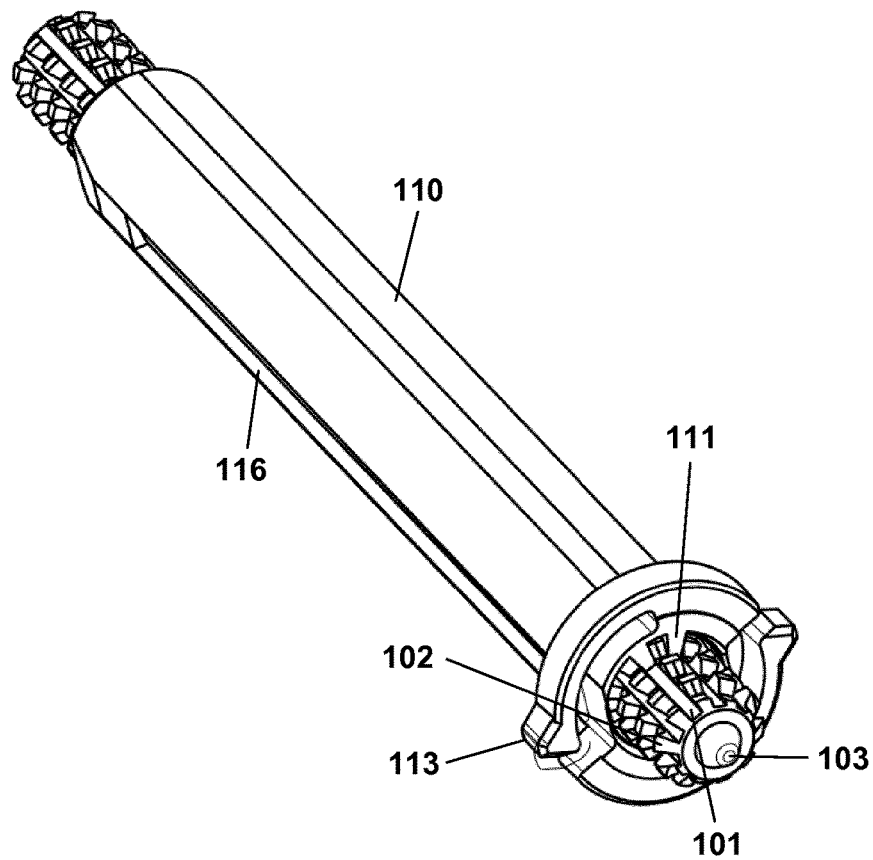

Turning to FIGS. 3A and 3B an exemplary embodiment of the present invention will be described. As described in detail above, when rotationally arranging the ratchet tube in one of its rotational pre-defined assembly positions, the resulting axial position of the piston rod will in most cases result in an air gap being created between the piston rod distal end and the piston washer.

In accordance with the invention the piston rod comprises an outer thread and at least one outer drive structure, and the drive member in which the piston rod is arranged comprises at least one inner drive structure. The drive structures can be provided in variety of configurations as long the number and circumferential spacing of the outer and inner drive structures allow the piston rod to be mounted in at least three different rotational positions in which the piston rod and drive member are in axially sliding but rotationally locked engagement.

As appears, in a simple configuration the piston rod or the drive member comprises a single drive structure and the other part comprises three drive structures, wherein the drive structure(s) on at least one of the components has/have a longitudinal configuration adapted to cooperate with a "punctual" structure on the other component.

FIG. 3A shows in a specific embodiment an assembly of a modified piston rod 100 and a correspondingly modified ratchet tube 110 which are in axially free but rotationally locked engagement with each other via a multi-splined interface. The piston rod comprises a threaded outer surface 102 adapted to engage a correspondingly threaded bore in a nut member, as well as a pointed distal end 103 adapted to engage a proximal surface of a piston washer. In the shown embodiment the ratchet tube is provided with 4 axially extending spline ridges 111 arranged as two opposed pairs of ridges, the ridges being adapted to engage four of 12 corresponding spline grooves 101 formed equidistantly in the threaded surface 102 of the piston rod 100, this allowing the ratchet tube to be mounted in 12 different rotational positions on the piston rod instead of two as described above. Having 12 potential rotational mounting positions instead of two allows the ratchet tube to be mounted on a piston rod, which has been rotated into engagement with the piston washer, in a rotational position which on average is closer to one of the two pre-defined mounting positions. As appears, when the ratchet tube is mounted closer to one of its predefined rotational positions, only a minor rotational adjustment will be necessary resulting on average in a smaller axial retraction of the piston rod and thus creation of a smaller air gap. Although it normally would be more desirable to retract the piston rod and create an air gap instead of moving the piston rod distally and thereby pressurize the cartridge, it may be acceptable to do this in cases where only a small amount of rotational adjustment is necessary, this resulting in full removal of the air gap. Thus, depending on the number of pre-determined rotational position for a given assembly it may be desirable for each individual assembly to be able to decide whether to move the piston rod distally and thereby pressurize the cartridge, or to move the piston rod proximally and thereby create an air gap, e.g. by using a vision system during the assembly.

In the shown embodiment the number of spline ridges is four and the number of spline grooves is 12, however, the number of spline ridges may differ from this exemplary embodiment. Further, the ratchet tube 110 is provided with a pair of opposed slots 116 adapted to cooperated with a pair of hook portions on the corresponding connector tube (not shown), this being a reversed arrangement compared to the embodiment of FIG. 1, as well as a pair of opposed ratchet arms 113 at the distal end.

In alternative embodiments the force transmitting rotational engagement between the ratchet tube and the piston rod may be based on essentially planar surfaces instead of splines, this as used in the embodiment described with reference to FIG. 1. Whereas the embodiment of FIG. 1 uses a single pair of opposed drive surfaces a larger number of drive surfaces may be provided on the piston rod. As for the above-described embodiment comprising splines, the number of driving surfaces on the ratchet tube inner surface may be smaller than the number of drive surfaces on the piston rod.

The optimal number and configuration of splines or drive surfaces will depend on a number of parameters, e.g. the characteristics of the piston rod thread, the diameters of the components, the desired amount of force to be transmitted, and the tolerances achievable with the given manufacturing methods for the components.

Turning to FIGS. 4A-4C the steps of an assembly procedure for a cartridge-piston rod sub-assembly 150 incorporating the components of the assembly of FIG. 3A will be described.

FIG. 4A shows a cartridge holder 120 arranged in a vertical position and in which a drug-filled cartridge 130 has been inserted. A piston washer 139 has been arranged on top of the cartridge piston. The cartridge holder comprises an opposed pair of proximally extending flanges 121 each provided with a slot 122 adapted to receive a corresponding hook portion 142 of a nut member 140 in snapping engagement as seen in FIG. 4B. When the nut member 140 has been mounted in the cartridge holder the piston rod 100 is inserted into the nut member threaded bore 144 and rotated distally until the distal end of the piston rod engages the piston washer. Depending on the specific design of the thread surfaces and materials of the components the piston rod may be moved distally by e.g. gravity or an applied force. When the piston rod 100 has been fully seated in touching engagement with the piston washer 139 the ratchet tube 110 is mounted onto the piston rod 100 in splined engagement therewith. In the shown embodiment the ratchet tube 110 can be mounted in 12 different rotational positions on the piston rod 100, however, as the ratchet tube has two predefined rotational mounting positions with 180 degrees rotational off-set, this provides six potential rotational mounting positions of the ratchet tube 110 spaced 30 degrees apart.

As the actual axial position of the piston in a given cartridge will vary, the rotational position of the engaged piston rod will correspondingly vary for an individual cartridge assembly. Thus, when mounting the ratchet tube 110 on the piston rod 100, the ratchet tube will have to be rotated away a given number of degrees from its predefined rotational mounting position to allow the ratchet tube splines to engage the piston rod splines. As described above, it may normally be desirable to retract the piston rod and create an air gap instead of moving the piston rod distally and thereby pressurize the cartridge, however, it may be acceptable to do this in cases where a small amount of rotational adjustment is necessary, this resulting in full removal of the air gap. Thus, depending on how far the piston rod is positioned rotationally from one of the 12 rotational positions that would allow the ratchet tube 110 be mounted directly in a predefined rotational position, the ratchet tube may be mounted in one of two alternative rotational positions, the first position requiring the ratchet tube to be rotated in a first direction to move the piston rod proximally and thereby create an airgap, the second position requiring the ratchet tube to be rotated in the opposed second direction to move the piston rod distally and thereby pressurize the cartridge. When the partially mounted ratchet tube has been rotated to a predefined rotational position the ratchet arms 113 will also be in alignment with the nut member ratchet array 143, this allowing the ratchet tube to be moved into its fully mounted proximal position as shown in FIG. 4C.

Although not part of the present invention, FIG. 4B shows a circumferential snap ring 123 and one of two opposed rotational positioning grooves 141 allowing the driver sub-assembly to be mounted on the cartridge sub-assembly in one of two predefined and 180 degrees off-set rotational positons with a housing window in rotational alignment with one of the two opposed cartridge inspection window areas 124.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A method of assembling a cartridge-piston rod sub-assembly for a drug delivery device, comprising the steps of:
   (i) providing an assembly comprising:
      a cartridge with an axially displaceable piston, the piston comprising a proximally facing free surface,
      a cartridge holder in which the cartridge is arranged, and
      a nut portion arranged proximally of the piston and comprising a threaded bore,
   (ii) providing a threaded piston rod comprising at least one outer drive structure and a distal end,
   (iii) providing a drive member comprising at least one inner drive structure, the number and circumferential spacing of the outer and inner drive structures allowing the piston rod to be axially received in at least three different rotational positions in which the piston rod and the drive member are in axially sliding but rotationally locked engagement, the drive member having at least one pre-determined rotational position relative to the cartridge holder,
   (iv) inserting the piston rod in the nut portion threaded bore and rotating the piston rod until the piston rod distal end engages, directly or indirectly, the cartridge piston,
   (v) mounting the drive member on the piston rod in a rotational position closest to at least one pre-determined rotational position, and
   (vi) rotating the drive member to the at least one pre-determined rotational position,
   wherein one of the at least three different rotational positions comprises one of:
      (a) the piston rod comprises at least three outer drive structures and the drive member comprises at least one inner drive structure,
      (b) the piston rod comprises at least one outer drive structure and the drive member comprises at least three inner drive structures, or
      (c) the piston rod comprises at least three outer drive structures and the drive member comprises at least three inner drive structures, and either the outer drive structure(s), the inner drive structure(s), or both the outer and inner drive structure(s) has/have a longitudinal configuration.

2. The method of assembling as in claim 1, wherein in step (iv) the drive member is rotated to further advance the piston rod when rotated to at least one pre-determined rotational position.

3. The method of assembling as in claim 1, wherein in step (iv) the drive member is rotated to retract the piston rod when rotated to at least one pre-determined rotational position.

4. The method of assembling as in claim 1, wherein in step (vi) the drive member has a first axial position in which the drive member is freely rotatable relative to the cartridge holder, and a second axial position in which the drive member is rotationally locked relative to the cartridge holder.

5. The method of assembling as in claim 4, wherein the rotational lock is provided by a one-way ratchet arranged between the drive member and the nut portion preventing rotation of the drive member relative to the nut portion in a first direction, and allowing rotation in the opposite direction when a certain force limit is exceeded.

6. A drug delivery device comprising:
a cartridge comprising a cylindrical body portion defining an axial orientation, an outlet portion and an axially displaceable piston,
a housing,
an expelling arrangement comprising:
a piston rod adapted to engage and axially displace, directly or indirectly, the cartridge piston in a distal direction to thereby expel a dose of drug from the cartridge, the piston rod comprising:
an outer thread, and
at least one outer drive structure,
a nut portion non-rotationally coupled to the housing and comprising a threaded bore receiving the piston rod in threaded engagement,
a drive member in which the piston rod is arranged, comprising at least one inner drive structure, the number and circumferential spacing of the outer and inner drive structures allowing the piston rod to be mounted in at least three different rotational positions in which the piston rod and the drive member are in axially sliding but rotationally locked engagement, and
a drive arrangement allowing a user to rotate the drive member to thereby expel the dose of drug from the cartridge as the piston rod is rotated and moved axially through the nut portion, and
wherein one of the at least three different rotational positions comprises one of:
(a) the piston rod comprises at least three outer drive structures and the drive member comprises at least one inner drive structure,
(b) the piston rod comprises at least one outer drive structure and the drive member comprises at least three inner drive structures, or
(c) the piston rod comprises at least three outer drive structures and the drive member comprises at least three inner drive structures, and
either the outer drive structure(s), the inner drive structure(s), or both the outer and inner drive structure(s) has/have a longitudinal configuration.

7. The drug delivery device as in claim 6, wherein the expelling arrangement further comprises:
a dose setting member rotatable from an initial position to a set position corresponding to a set dose, and
an actuation member actuatable to rotate the drive member corresponding to the set dose.

8. The drug delivery device as in claim 7, wherein:
the actuation member is moved proximally during dose setting from an initial position to a set position corresponding to the rotationally set dose, and
the actuation member is actuatable by distal movement from the set position to the initial position.

9. The drug delivery device as in claim 7, wherein the expelling arrangement further comprises:
a drive spring strained during dose setting corresponding to the set dose,
wherein the drive spring is released to rotate the drive member corresponding to the set dose when the actuation member is actuated.

10. The drug delivery device as in claim 6, wherein the outer and inner drive structures are in the form of corresponding spline structures.

11. The drug delivery device as in claim 6, wherein the outer and inner drive structures are in the form of corresponding primarily planar surfaces.

12. The drug delivery device as in claim 6, wherein a one-way ratchet is arranged between the drive member and the nut portion preventing rotation of the drive member relative to the nut portion in a first direction, and allowing rotation in the opposite direction when a certain force limit is exceeded.

13. A cartridge-piston rod sub-assembly for a drug delivery device, comprising:
a cartridge with an axially displaceable piston, the piston comprising a proximally facing free surface,
a cartridge holder in which the cartridge is arranged,
a nut portion non-rotationally coupled to the cartridge holder and comprising a threaded bore adapted to receive the piston rod in threaded engagement,
a piston rod received in the threaded bore and adapted to engage and axially displace, directly or indirectly, the cartridge piston in a distal direction to thereby expel a dose of drug from the cartridge, the piston rod comprising:
an outer thread, and
at least one outer drive structure,
a drive member in which the piston rod is arranged, comprising at least one inner drive structure, the drive member having at least one pre-determined rotational position relative to the cartridge holder,
wherein, the number and circumferential spacing of the outer and inner drive structures allows the piston rod to be mounted in at least three different rotational positions in which the piston rod and the drive member are in axially sliding but rotationally locked engagement, and
wherein one of the at least three different rotational positions comprises one of:
(a) the piston rod comprises at least three outer drive structures and the drive member comprises at least one inner drive structure,
(b) the piston rod comprises at least one outer drive structure and the drive member comprises at least three inner drive structures, or
(c) the piston rod comprises at least three outer drive structures and the drive member comprises at least three inner drive structures, and either the outer drive structure(s), the inner drive structure(s), or both the outer and inner drive structure(s) has/have a longitudinal configuration.

* * * * *

UNITED STATES PATENT AND TRADEMARK OFFICE
CERTIFICATE OF CORRECTION

| | |
|---|---|
| PATENT NO. | : 11,511,046 B2 |
| APPLICATION NO. | : 16/754982 |
| DATED | : November 29, 2022 |
| INVENTOR(S) | : Daniel Knudsen et al. |

It is certified that error appears in the above-identified patent and that said Letters Patent is hereby corrected as shown below:

On the Title Page

Item (57) Line number 5, please replace with the following:
"a drive member on the piston rod in a rotational position"

Signed and Sealed this
Twentieth Day of June, 2023

*Katherine Kelly Vidal*

Katherine Kelly Vidal
*Director of the United States Patent and Trademark Office*